United States Patent
Allen et al.

(10) Patent No.: US 6,689,376 B2
(45) Date of Patent: Feb. 10, 2004

(54) DIRECT FEEDING OF SEAWEED SUPPLEMENT TO CATTLE AND SWINE TO ENHANCE CARCASS QUALITY

(75) Inventors: Vivien Gore Allen, Lubbock, TX (US); Kevin R. Pond, Wolfforth, TX (US)

(73) Assignee: Texas Tech University, Lubbock, TX (US)

(*) Notice: Subject to any disclaimer, the term of this patent is extended or adjusted under 35 U.S.C. 154(b) by 33 days.

(21) Appl. No.: 10/103,914

(22) Filed: Mar. 25, 2002

(65) Prior Publication Data

US 2002/0142024 A1 Oct. 3, 2002

Related U.S. Application Data

(60) Division of application No. 09/694,273, filed on Oct. 24, 2000, now Pat. No. 6,391,331, which is a continuation-in-part of application No. 09/469,176, filed on Dec. 21, 1999, now Pat. No. 6,338,856, which is a continuation-in-part of application No. 09/032,104, filed on Feb. 27, 1998, now Pat. No. 6,342,242.

(51) Int. Cl.[7] ................................................ A23K 1/00

(52) U.S. Cl. .................. 424/442; 424/439; 424/195.17; 424/548; 426/2

(58) Field of Search .............................. 424/439, 442, 424/195.17, 548; 426/2, 655, 623

(56) References Cited

U.S. PATENT DOCUMENTS

| | | | |
|---|---|---|---|
| 5,229,118 A | 7/1993 | Campbell | 424/195.1 |
| 5,843,762 A | 12/1998 | Moll | 435/257.1 |
| 6,270,812 B1 | 8/2001 | Allen et al. | 426/2 |
| 6,312,709 B1 | 11/2001 | Allen et al. | 424/438 |
| 6,338,856 B1 | 1/2002 | Allen et al. | 424/442 |
| 6,342,242 B1 | 1/2002 | Allen et al. | 424/439 |

FOREIGN PATENT DOCUMENTS

JP 54-040176 3/1979

OTHER PUBLICATIONS

Kotrbacek et al Effects of Algae—Nov. 1995 Zivocisna Vyroba—GZPI V. 40 (11) p. 579–522.*

Harrison—Dissertation Abstracts U.F. vol. 47/05–B Waste Grown Micro Algae—p. 1804 1986.*

Kim, C. S., et al., The Effect of Dietary Sargassum–Natans and Ascophyllum–Nodosum on Salmonella Gallinarum Infection in Chicks, BIOSIS (AN 1969:8848).

Herskoviz, R., et al., Differential effects of Polysulfated polysaccharide on experimental encephalomyelitis, proliferation of autoimmune T cells, and inhibition of heparanase activity, BIOSIS (AN 1996:22174).

Matsuzaki, S., et al., Application of seaweeds to human nutrition and medicine CA (AN97:4974) 1981.

Nishizawa, K., Seaweed as food for controlling diseases in elderly patients, CAPLUS (AN 1998:590009).

Kim, C. S., The Effects of Dietary Sargassum–Natans and Ascophyllum–Nodosum on Salmonella–Gallinarum Infection in Chicks, BIOSIS (AN 1973:82740).

(List continued on next page.)

*Primary Examiner*—Neil S. Levy

(57) ABSTRACT

Seaweed supplement, e.g., seaweed extract or seaweed meal is directly fed to cattle or pigs in amount of 0.01 to 5% by weight of diet to enhance carcass quality. The enhancement of carcass quality for cattle is manifested by increased quality grade, increased marbling, increased ribeye area and decrease in yield grade in meat obtained on slaughter compared to where seaweed supplement is not fed. The enhancement of carcass quality for swine is manifested by increased marbling, increased firmness and decreased cooler shrink in meat obtained on slaughter compared to where seaweed supplement is not fed.

9 Claims, 8 Drawing Sheets

OTHER PUBLICATIONS

Charreau, B., et al., Efficiency of fucans in protecting porcine endothelial cells against complement activation and lysis by human serum, BIOSIS (AN 1997:190627).

Blondin, C., et al., Relationships between chemical characteristics and anticomplementary activity of fucans, BIOSYS (AN 1996:188236).

Ren, D., et al., Study on Antihypertensive and Antihyperelipidemic Effects of Marine Algae, BIOSIS (AN 1994:487915).

Klinger, M. M., et al., Anti–HIV Activity of Sulfated Polysaccharides from the Brown Seaweed Ascophyllum nodosum, DRUGU M (AN 91–25081) '91.

Blunden, G., et al., Medicinal and Pharmaceutical Uses of Algae, DRUGU TMPS (AN 87–01915) (1987).

Brochure titled Field Trial Summaries, Impact of Acadian Seaplants Seaweed on Agricultural Crops, Acadian Seaplants Limited, Nova Scotia, Canada (undated) Jan. 1992.

Product and Technical Information, Ascophylluns nodosum Kelp Meal and Flour, Acadian Seaplants Limited, Nova Scotia, Canada (Jan. 10, 1998).

Information Sheet of Acadian Seaplants Seaweed Extract, Acadian Seaplants Limited, Nova Scotia, Canada, Jan. 8, 1998.

Brochure titled Acadian Seaplants Seaweed Extract Soluble Powder or Liquid, Acadian Seaplants Limited, Nova Scotia, Canada (undated) Jan. 1998.

Information Sheet titled Product and Technical Information, General Home and Garden Use, Acadian Seaplants Limited, Nova Scotia, Canada (Sep. 5, 1998).

Brochure titled Acadian on Grapes, Grower's Success Series, Acadian Seaplants Limited, Nova Scotia, Canada (undated) '98.

Brochure titled Acadian Seaplants Kelp Meal (100% Ascophyllum nodosum) For Soil Applications, Acadian Seaplants Limited, Nova Scotia, Canada (undated) Jan. 1998.

Fike, J. H., et al., Proc. 1997 Amer. Forage and Grassl. Counc., Georgetown, TX, 6:168–172.

Schmidt, R. E., et al., Proc. 1997 Amer. Forage and Grassl. Counc., Georgetown, TX, 6:158–162.

Coelho, R. W., et al., Proc. 1997 Amer. Forage and Grassl. Counc., Georgetown, TX, 6:163–167.

Allen, V. G., et al., Proc. 1997 Amer. Forage and Grassl. Counc., Counc., Georgetown, TX, 6:168–172.

Saker, K. E., et al., Proc. 1997 Amer. Forage and Grassl. Counc., Georgetown, TX, 6:178–182.

Hobbs, D., The New Farm May/Jun. 1994, 26–28.

Klober, K., Small Farm Today, Aug. 1996, p. 10.

Hobbs, D., "The Quest for a Water Soluble Mineral" (undated) '96.

Hobbs, D., "Kelp Cures Copper" (undated).

Morrison, F. B., Fields and Feeding, The Morrison Publishing Company, Ithaca, NY (1957), p. 554.

Dennis, S. B., et al., J. Anim. Sci. 76, 2687–2693 (1998).

Fike, J. H., Masters Thesis titled Influence of Seaweed Extract and Other Plant Growth Regulators.

Persistence and Quality of Tall Fescue and Their Potential to Alleviate Tall Fescue Toxicity to Livestock (1995).

Hobbs, D., "Soil Amending Attributes of Kelp Meal" (undated) 96.

Hobbs, D., "Benefit of Foliar Applied Seaweed Extract" (undated) 96.

Sen, T. L., Seaweed and Plant Growth (1987), pp. 7–4, 7–5.

Buttery, S., Influence of Acremonium Coenophialum on Fescue Arundinacea Growth, Chemical Composition, Digestibility and Tall Fescue Toxicities; Ph.D. Dissertation, 1989, abstract and pp. 36, 84 and 86.

Okai, Y., et al., J. Sci. Food Agric. 72, 455–460 (1966).

Okai, Y., et al., J. Sci. Food Agric. 76, 56–62 (1998).

Theriault, L., News Release sent Oct. 12, 2000 and Oct. 13, 2000, titled "Research Partnership Results in Feed Industry Patents and Exciting New Feed Products".

Woodward, L., Vistas, Texas Tech Research, Fall 1999, vol. 8, No. 1, pp. 20–25.

Saker, K. E., et al., J. Anim. Sci. 76, 2694–2700 (1998).

Correale, K. K., Meat Science 18, 161–172 (1986).

* cited by examiner

Control vs treated (P<.17).

Extract differs from control (P<.17)
Meal long differs from control (P<.03).

DIRECT FEEDING OF SEAWEED SUPPLEMENT TO CATTLE AND SWINE TO ENHANCE CARCASS QUALITY

CROSS-REFERENCE TO RELATED APPLICATIONS

This is a division of U.S. patent application No. 09/694,273, filed Oct. 24, 2000 now U.S. Pat. No. 6,391,331, which is a continuation-in-part of U.S. patent application No. 09/469,176 filed Dec. 21, 1999, now U.S. Patent No. 6,338,856, which in turn is a continuation-in-part of U.S. patent application No. 09/032,104 filed Feb. 27, 1998, now U.S. Pat. No. 6,342,242.

TECHNICAL FIELD

The invention herein is directed to enhancing the carcass quality of cattle and swine.

BACKGROUND OF THE INVENTION

We turn first to carcass quality of cattle, i.e., the quality of beef obtained from cattle. Beef is typically obtained from cattle (beef cattle or diary cattle) that have grazed in pastures and have been fed in feedlots. About two years after birth, the animals are slaughtered and primal cuts are obtained. The primal cuts are usually vacuum packaged to preserve freshness, and the vacuum packaged primal cuts are sent to supermarkets or other meat distribution businesses where the vacuum packaging is removed and the primal cuts are cut into smaller cuts which are repackaged or displayed in a case for sale. The price obtained on sale of the cattle is related to carcass quality which can be predicted in advance of slaughter (e.g., on the basis of ultrasonic measurement). The price obtained on sale of the meat also is related to carcass quality as determined by evaluation of the meat. The higher the carcass quality is, the higher the price obtained is.

We turn now to the carcass quality of swine, i.e., the quality of the pork obtained on slaughter. The typical life cycle for swine for pork production consists of remaining with the mother for 14 to 28 days, and being weaned and being placed in a nursery for three to five weeks, being moved to a finishing barn where they are kept until reaching 220 to 275 pounds (three to four months), and finally transported for slaughter. The price obtained for the swine and for the pork therefrom is related to carcass quality in that the higher the carcass quality is, the higher the price obtained is.

SUMMARY OF THE INVENTION

It has been discovered that directly feeding seaweed supplement to cattle and swine enhances carcass quality.

One embodiment of the invention herein, denoted the first embodiment of the invention herein, is directed to a method of enhancing carcass quality in cattle, comprising (a) directly feeding seaweed supplement to cattle in a feedlot in a carcass quality improving amount thereby to cause carcass quality improvement as manifested by increased quality grade, marbling and ribeye area and decreased yield grade in meat obtained on slaughter of the cattle compared to where seaweed supplement is not fed and (b) determine at least one of quality grade, marbling, ribeye area and yield grade.

Quality grades, an industry standard, are based on marbling determinations by a skilled evaluator. Marbling scores are based on a scale ranging from 200 to 1,000 according to the following amounts of fat marbling as indicated in Table 1 below.

TABLE 1

| Marbling Score | Amount of Marbling |
| --- | --- |
| 1,000 | abundant |
| 900 | moderately abundant |
| 800 | slightly abundant |
| 700 | moderate |
| 600 | modest |
| 500 | small |
| 499–400 | slight |
| 399–300 | traces |
| 299–200 | practically devoid |

The relation of quality grades and marbling scores are set forth below in Table 2.

TABLE 2

| Number | Name | Relation to Marbling Score |
| --- | --- | --- |
| 15 | High Prime | >999 |
| 14 | Average Prime | >899 |
| 13 | Low Prime | >799 |
| 12 | High Choice | >699 |
| 11 | Average Choice | >599 |
| 10 | Low Choice | >499 |
| 9 | High Select | >449 |
| 8 | Low Select | >399 |
| 7 | High Standard | >339 |
| 6 | Average Standard | >269 |
| 5 | Low Standard | 200–269 |

Ribeye area is the area of the longissimus dorsi (and is determined in square inches or square centimeters) according to a standard in the industry by visual estimation or actual measurement.

Yield grades are an industry standard and are determined according to the formula:

$$\text{Yield grade} = (\text{hot carcass weight in pounds} - 600) \times 0.0038 + (11 - \text{ribeye area in square inches}) \times 0.32 + (\text{kidney, pelvic and heart fat in square inches} - 3.5) \times 0.2 + \text{adjusted preliminary yield grade}).$$

The hot carcass weight is the weight directly after slaughter after evisceration and removal of the hide, head, feet and internal organs. The kidney pelvic and heart fat is determined by visual estimation. The adjusted preliminary yield grade is determined by a USDA grader or trained evaluator.

Preferably, the method of the first embodiment herein is carried out to increase quality grade at least one grade level, e.g., from 6 to 7, to increase marbling score at least 20, to increase ribeye area at least 0.1 square inches and to decrease yield grade at least 0.02 compared to where seaweed supplement is not fed.

We turn now to another embodiment, denoted the second embodiment of the invention herein. This embodiment is directed to a method of enhancing carcass quality in swine, comprising directly feeding seaweed supplement to swine in a carcass quality improving amount thereby to cause carcass quality improvement as manifested by increased marbling, increased firmness and decreased cooler shrink.

The marbling referred to for the second embodiment is fat marbling in the longissimus dorsi taken at the tenth rib and is based on a scale of 1 to 5 per the National Pork Producer Council's Guidelines for Carcass Evaluation, and is determined by a skilled grader. Increased marbling is considered beneficial.

The firmness referred to for the second embodiment is based on the scale of 1 to 8, with 8 being extremely firm and 1 being extremely soft with levels between having firmnesses between in equal increments and is determined by a skilled evaluator. The higher the firmness score, the better is considered the resulting pork.

The cooler shrink referred to for the second embodiment is the difference in weight between the hot carcass weight and the weight after cooling to 40° F. in pounds. The weight loss in cooling is due to loss of moisture in the cooler. The hot carcass weight is the same as the case for beef. The less the cooler shrink, the better is considered the meat.

Preferably, the method of the second embodiment herein is carried out to increase marbling at least 0.05, increase firmness at least 0.2 and decrease cooler shrink at least 0.2 compared to where seaweed supplement is not fed.

DETAILED DESCRIPTION

Figure 1:
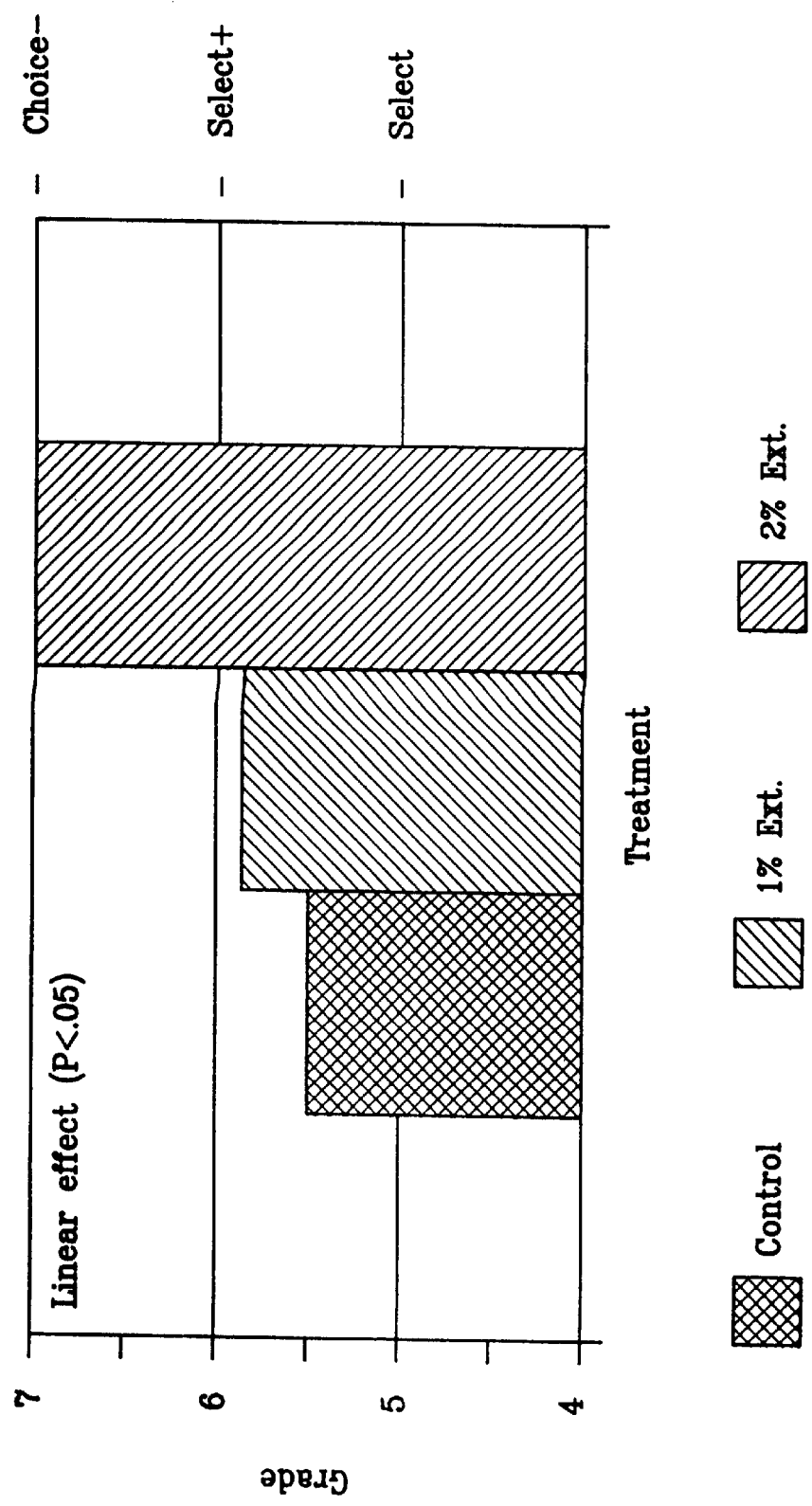
FIG. 1 depicts graphs showing quality grades obtained on direct feeding of seaweed extract at 1% of diet and at 2% of diet to cattle versus control and shows results of Example I.

We turn now to the seaweed supplement used in both of the embodiments herein.

The seaweed from which the seaweed supplement is obtained can be from any of the various seaweed plant classifications, preferably those that have been utilized in agriculture and include seaweeds from the plant orders Laminariaceae, Fucaceae and Gigartinaceae. Genus groups include Ascophyllum, Laminaria, Durvillea, Macrocystis, Chondrus and Ecklonia. The seaweed for the preferred seaweed supplement herein is from the genus Ascophyllum which belongs to the order Fucaceae and is *Ascophyllum nodosum*. *Ascophyllum nodosum* is a brown seaweed which grows along the North Atlantic shorelines of Canada, the United States, and Europe.

The seaweed supplement can be, for example, seaweed extract or seaweed meal.

We turn now to seaweed supplement which is seaweed extract.

Seaweed extract is water soluble and can be obtained by alkaline hydrolysis extraction. A preferred seaweed extract is obtained by alkaline hydrolysis extraction from *Ascophyllum nodosum*; commercial products of this kind are available from Acadian Seaplants Limited of Nova Scotia Canada, and are sold under the tradenames Acadian Soluble Seaweed Extract Powder (powder form), Acadian Liquid Seaweed Concentrate (liquid form), Tasco™-Ex (powder form) and Tasco™-Forage (powder form). Acadian Soluble Seaweed Extract Powder, Tasco™-Ex and Tasco™-Forage have the same composition. Acadian Soluble Seaweed Extract Powder is made up of brownish-black crystals, has a seaweed-like odor, is 100% soluble in water and has a pH of 10–10.5 in water and typical analysis shows by weight 6.5% maximum moisture, 45–55% organic matter, 45–55% ash (minerals), 1.0–2.0% total nitrogen (N), 2.0–4.0% available phosphoric acid ($P_2O_5$), 18.0–22.0% soluble potash ($K_2O$), 1.0–2.0% sulfur (S), 0.2–0.5% magnesium, 0.1–0.2% calcium, 3.0–5.0% sodium, 75–150 ppm boron, 75–250 ppm iron, 8–12 ppm manganese, 1–10 ppm copper, 25–75 ppm zinc; alginic acid, mannitol, and laminarin carbohydrates; cytokinin, auxin and gibberellin growth promoters; and the following average grams of amino acid per 100 grams of protein: alanine, 3,81; arginine, 0.22; aspartic acid, 5.44; cystine, trace; glutamic acid, 7.69; glycine, 3,16; histidine, 0.42; isoleucine, 1.94; levcine, 4.84; lysine, 1.33; methonine, 1.39; phenylalanine, 2.82; proline, 4.42; serine, 0.14; threonine, 1.27; tyrosine, 1.80, and valine, 3.46.

We turn now to seaweed supplement which is seaweed meal or flour.

The seaweed meal or flour can be obtained by dehydrating the seaweed, for example, by solar drying followed by low heat finish drying and processing the dehydrated material into a granular meal or four. A preferred seaweed meal is obtained from *Ascophyllum nodosum* and is available from Acadian Seaplants Limited of Nova Scotia, Canada, and is sold under the tradenames Acadian Kelp Meal and Tasco™-14. Acadian Kelp Meal and Tasco™-14 have the same composition. A typical analysis of Acadian Kelp Meal shows the following approximate weight percentages: moisture 12.0%, crude protein 6.0%, crude fiber 6.0%, ash (minerals) 22.0%, fat 20%, and carbohydrates 52.%. Analysis of Acadian Kelp Meal for carbohydrates gives by weight 18.0–27.0% alginic acid, 3.8–8.0% mannitol, 2.0–5.0% laminarin, and 20.0–22.0other sugars. Analysis of Acadian Kelp Meal for minerals gives 50–150 ppm aluminum, 5–15 ppm barium, <1 ppm beryllium, 80–100 ppm boron, <1 ppm cadmium 1.0–3.0% calcium, 1.0–3.0% chloride, 1–2 ppm chromium, <1 ppm cobalt, 1–10 ppm copper, <1,000 ppm iodine, 100–500 ppm iron, <1 ppm lead, 0.5–1.0% magnesium, 10–50 ppm manganese, <1 ppm mercury, <2ppm molybdenum, <1 ppm nickel, 0.5–2.0% nitrogen, 0.1–0.2%phosphorus, 1.5–2.5% potassium, 3–4 ppm selenium, 2.4–4.0% sodium, 100–600 ppm strontium, 2.0–3.0% sulfur, <10 ppm tin, 1–10 ppm titanium, 2–6 ppm vanadium and 10–50 ppm zinc. Analysis of Acadian Kelp Meal for vitamins gives 0.1–0.4 ppm biotin, 30–60 ppm carotene, 0.1–0.5 ppm folic acid, 0.1–0.5 ppm folic acid, 10–30 ppm niacin, 5–10 ppm riboflavin, 1–5 ppm thiamin, 150–300 ppm tocopherols, 100–2,000 ppm vitamin C, <0.004 ppm vitamin $B_{12}$, and <10 ppm vitamin K. Analysis of the amino acid content for Acadian Kelp Meal gave the following expressed as grams of amino acid per 100 g of protein nitrogen: alanine 5.3, arginine 8.0, aspartic acid 6.9, cystine (trace), glycine 5.0, glutamic acid 10.0, histidine 1.3, isoleucine 2.8, leucine 4.6, lysine 4.9, methionine 0.7, phenylalanine 2.3, proline 2.6, serine 3.0, threonine 2.8, tryptophan (trace), tyrosine 0.9, and valine 3.7.

We turn now to the method of the first embodiment, that is the method of enhancing carcass quality in cattle, comprising directly feeding seaweed supplement to cattle in a feedlot in a carcass quality improving amount thereby to cause carcass quality improvement as manifested by increased quality grade, marbling and ribeye area and decreased yield grade in meat obtained on slaughter of the cattle compared to where seaweed supplement is not fed; and (b) determining at least one of quality grade, marbling, ribeye area and yield grade.

The seaweed supplement is directly fed to the cattle during the finishing period which typically is the 90–160 days before transportation to slaughter.

The cattle to which step (a) is applied, can weigh, for example, from about 550 to about 850 pounds when seaweed supplement is given initially and seaweed supplement can also additionally be given toward or at the end of the finishing period. The quality grade is affected more by feeding seaweed supplement early in the finishing period than at the end of the finishing period. At the end of the finishing period, the cattle typically weigh 1,200 to 1,300 pounds each.

Seaweed supplement is preferably fed for the first embodiment in an amount ranging from, for example, about 0.01 to 5% by weight of this diet for 5 to 40 days.

The seaweed supplement is fed, for example, in an amount ranging from 0.5 to 2.5% by weight of the diet for at least 10 days during the feedlot finishing period, e.g., for at least 10 days (e.g., 10–20 days) at the beginning of the feedlot finishing period or starting after completion of the receiving diets, e.g., starting about 30 days into the finishing period, and very preferably, also additionally, for at least 10 days (e.g., 10–20 days) at the end of the finishing period.

When the seaweed supplement is seaweed extract, it is preferably admixed into diet for direct feeding by inclusion at the time of feeding by top dressing on mixing into the feed at the time of feeding or by premixing at the time the diet ingredients are combined and is included in an amount of, e.g., 0.1 to 3% by weight (powder or liquid concentrate commercial products) of the diet.

When the seaweed supplement is seaweed meal, it is preferably admixed into diet for direct feeding by inclusion at the time the diet ingredients are mixed or by directed addition at the time of feeding, in amount of e.g., 0.01 to 5%, by weight of the diet.

The determinations in step (b) are standard in the industry.

Method of the first embodiment is shown in working examples to increase quality grade; marbling and ribeye area and to decrease yield grade.

We turn now to the method of the second embodiment, that is the method of enhancing carcass quality in swine, comprising directly feeding seaweed supplement to swine in a carcass quality improving amount thereby to cause carcass quality improvement as manifested by increased marbling, increased firmness and decreased cooler shrink in meat obtained on slaughter compared to when seaweed supplement is not fed, and (b) determining at least one of marbling, firmness and cooler shrink.

The seaweed supplement is preferably fed to piglets during part or all of the nursery period, i.e., after removal from the mother and before they are placed in a finishing barn.

The seaweed supplement is fed, for example, at least 5 days or at least 10 days when the piglets are in the nursery, e.g., the first 10 to 15 days at the beginning of the period, or the last 10 to 15 days at the end of the period when the piglets are in the nursery in an amount of 0.01 to 5% by weight of the diet, e.g., 0.5 to 1.5% by weight of the diet, e.g., in an amount of 1% by weight of the diet. In a working example hereinafter, good results are obtained also when seaweed meal is fed during the entire nursery period. Preferably, the seaweed supplement is fed for 5 to 28 days of the nursery period. The diet referred to can be any of the those normally fed to piglets in the nursery, e.g., 60–65% by weight milo (sorghum), 30–35% by weight soybean meal, and up to 5% by weight vitamins and minerals and other additives, e.g., growth promoter.

We turn now to the feeding of seaweed supplement in the second embodiment. When the seaweed supplement is seaweed extract, it is preferably admixed into diet for direct feeding by inclusion at the time of feeding by top dressing on mixing into the feed at the time of feeding or by premixing at the time the diet ingredients are combined and is included in an amount. e.g., of 0.1 to 3% by weight (powder or liquid concentrate commercial products) of the diet. When the seaweed supplement is seaweed meal, it is preferably admixed into diet for direct feeding at the time the diet ingredients are mixed or by directed addition at the time of feeding, in an amount of, e.g., 0.01 to 5% by weight of the diet.

The method of the second embodiment herein is shown in working Example III to increase marbling and firmness and to reduce cooler shrink.

The invention is illustrated in the following working examples.

In Examples I and II, the control diet consisted of a first receiving diet which was fed for two weeks (Receiving 1) followed by a second receiving diet (Receiving 2) which was fed for two weeks, followed by an intermediate diet for two weeks followed by a finishing diet for the remainder of the finishing period. The treatment diets supplemented the control diets in the treatment cases. The diets are set forth in Table 3 below where AS-700 is Aureo 5700 (a chlortetracycline plus sulfamethazine) which is a growth promotant for cattle, where Rumensin premix is an efficiency additive and where Tylosin premix is a growth promotant

TABLE 1

| | Diet | | | |
|---|---|---|---|---|
| | Percentage of Diet | | | |
| Item | Receiving 1 | Receiving 2 | Intermediate | Finishing |
| Steamflaked milo | 39.24 | 55.00 | 64.03 | 78.25 |
| Cottonseed hulls | 43.00 | 28.98 | 20.92 | 8.00 |
| Molasses, cane | 3.00 | 3.00 | 4.00 | 4.00 |

TABLE 1-continued

| | Diet | | | |
| | Percentage of Diet | | | |
| Item | Receiving 1 | Receiving 2 | Intermediate | Finishing |
|---|---|---|---|---|
| Fat | 2.80 | 2.60 | 2.45 | 2.80 |
| Cottonseed meal | 2.80 | 2.50 | 2.50 | .00 |
| Corn gluten meal | 2.80 | 2.00 | 1.30 | 2.15 |
| Blood meal | 2.80 | 2.00 | 1.30 | .00 |
| Calcium carbonate | .94 | 1.06 | 1.15 | 1.27 |
| Dicalcium phosphate | .35 | .20 | .12 | .00 |
| Urea | .20 | .30 | .40 | .60 |
| Potassium chloride | .00 | .10 | .23 | .47 |
| Trace mineral premix | .23 | .24 | .25 | .26 |
| Sodium chloride | .15 | .15 | .15 | .14 |
| Vitamin A premix | .38 | .38 | .38 | .38 |
| Vitamin E premix | .09 | .09 | .09 | .09 |
| Rumensin premix | .37 | .55 | .73 | 1.00 |
| Tylosin premix | .00 | .00 | .00 | .60 |
| AS-700 | .85 | .85 | .00 | .00 |

We turn now to working Example I.

EXAMPLE I

Twenty-four steers were fed a diet of 0, 1 or 2% seaweed extract (Acadian Soluble Seaweed Extract Powder) for 10 days, from November 14 to November 24, at the beginning of a finishing period extending until April 27 when the steers were slaughtered (eight steers per case). The steers weighed about 800 lbs. at the beginning of the period and 1,150 to 1,225 pounds at the end of the period.

Quality grades were determined and the results are shown in FIG. 1 where 1% Ext. and 2% Ext. respectively mean 1% seaweed extract by weight of diet and 2% seaweed extract by weight of diet. As shown in FIG. 1 administration of seaweed extract caused increase in quality grade and in the case of 2% seaweed treatment increase from select average to choice minus (i.e., from about 5.5 to 7).

Figure 2:
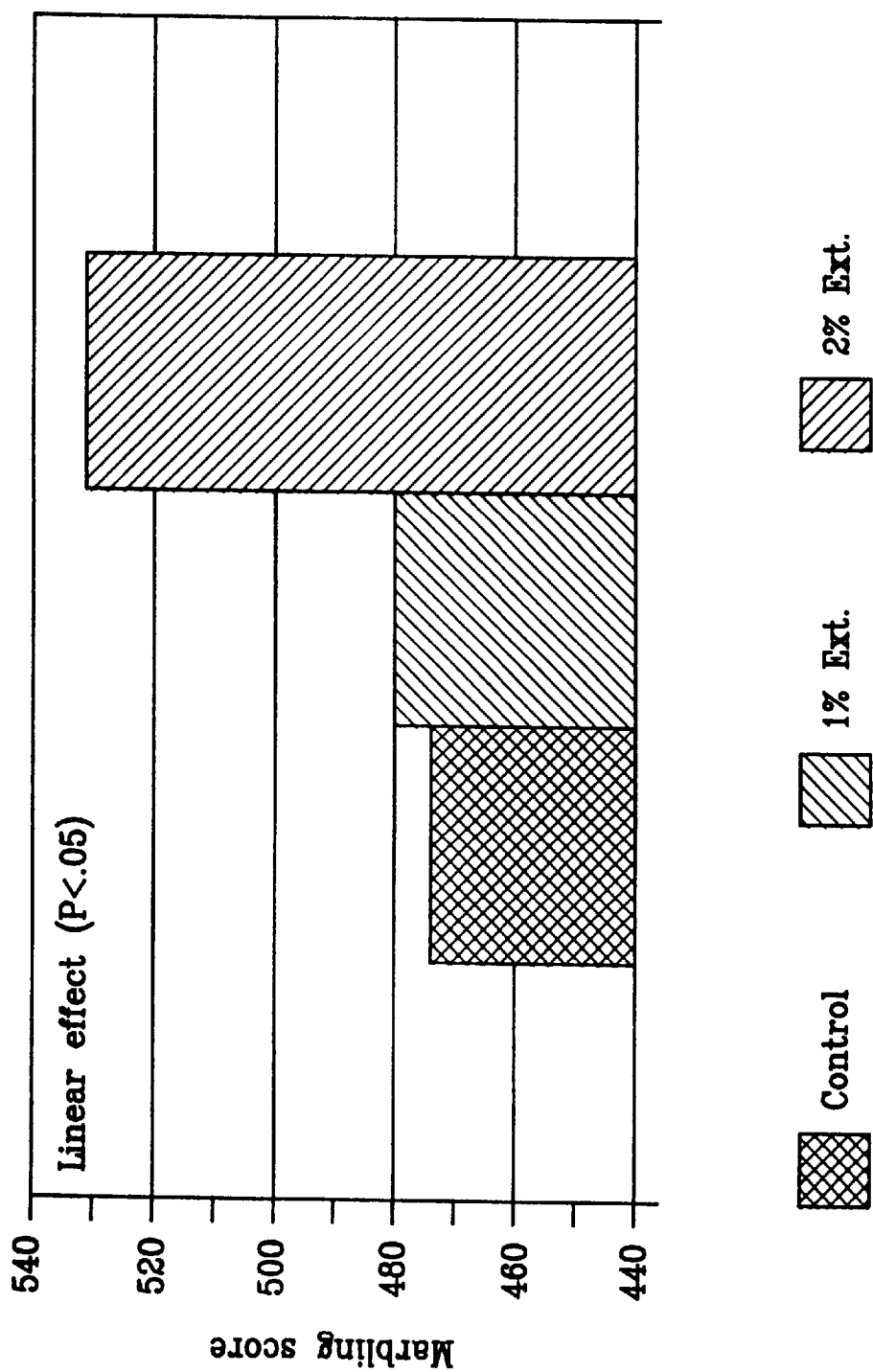
FIG. 2 depicts graphs showing marbling scores obtained on direct feeding of seaweed extract at 1% of diet and at 2% of diet to cattle versus control and shows results of Example I.

Marbling scores were determined and the results are shown in FIG. 2 where 1% Ext. and 2% Ext. respectively mean 1% seaweed extract by weight of diet and 2% seaweed extract by weight of diet. As shown in FIG. 2, seaweed extract administration caused increase in marbling score and in the case of 2% seaweed extract, the increase was from about 475 to bout 530.

Figure 3:
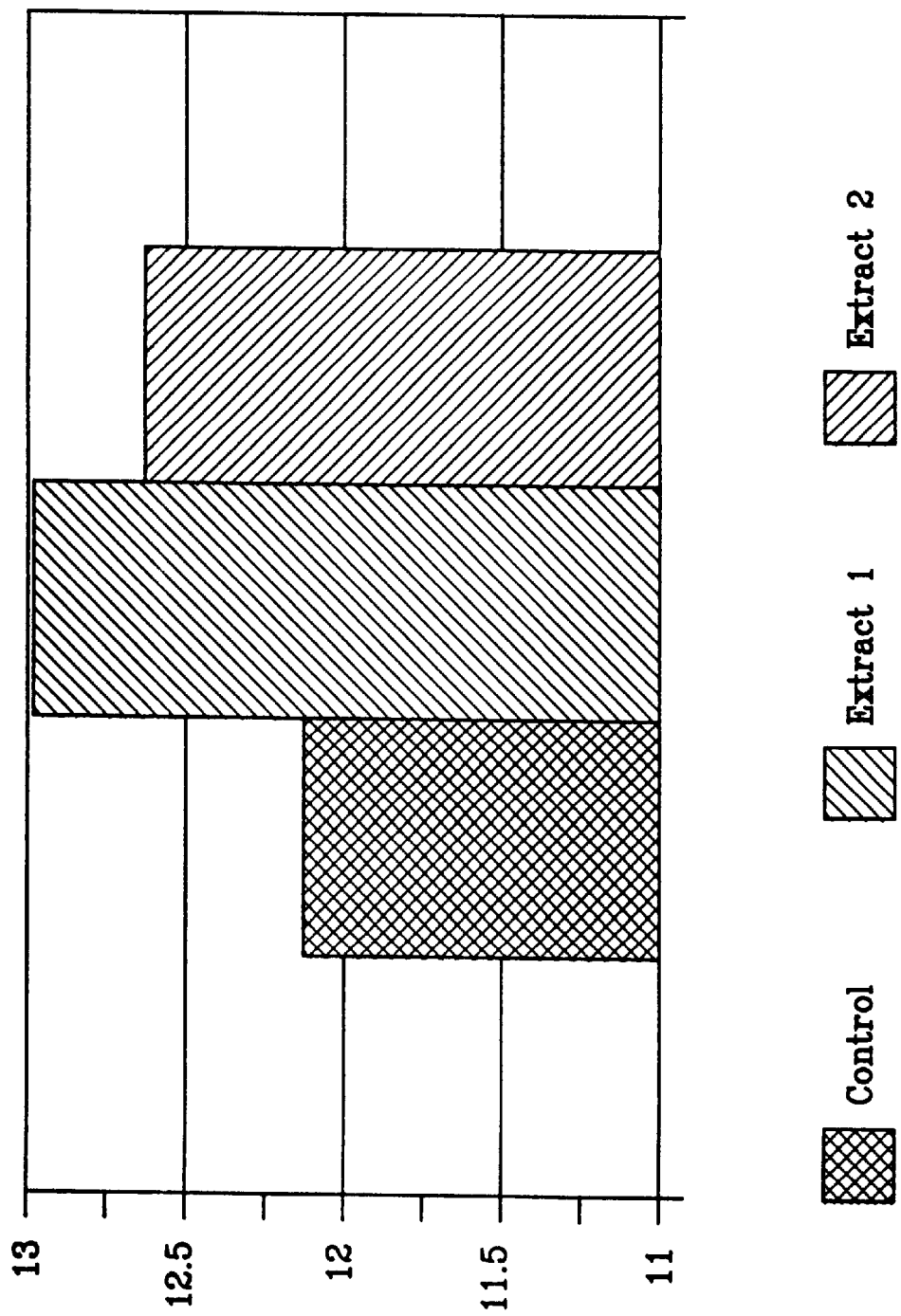
FIG. 3 depicts graphs showing ribeye area in square inches obtained on direct feeding of seaweed extract at 1% of diet and at 2% of diet to cattle versus control and shows results of Example I.

Ribeye areas in square inches were determined and results are shown in FIG. 3. As shown in FIG. 3, seaweed extract administration caused increase in ribeye area parameter and in the case of 1% seaweed extract, the increase was from about 12.2 inches to about 13 inches.

Figure 4:
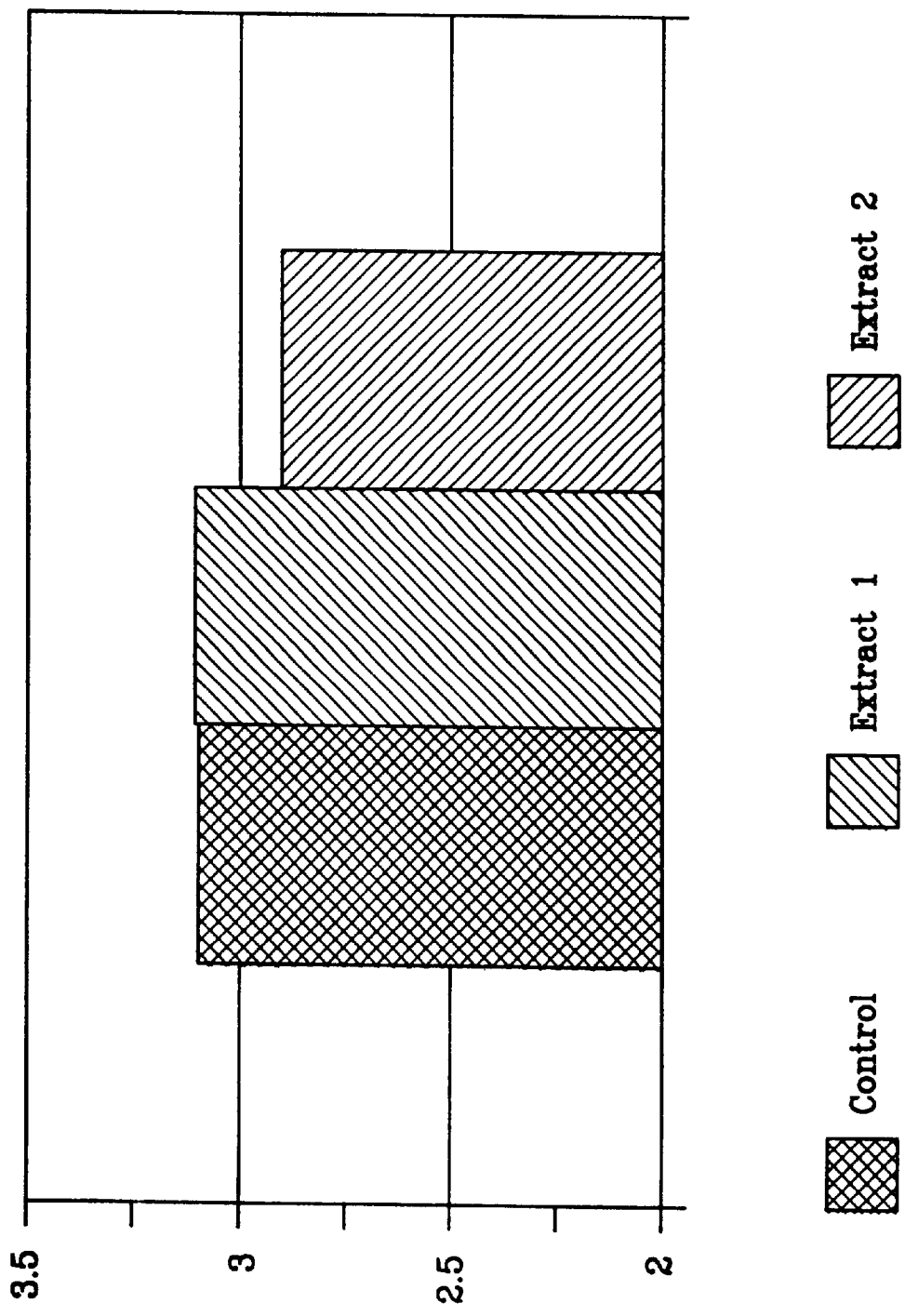
FIG. 4 depicts graphs showing yield grades obtained on direct feeding of seaweed extract at 1% of diet and at 2% of diet to cattle versus control and shows results of Example I.

Yield grades were determined and results are shown in FIG. 4. As shown in FIG. 4, seaweed extract administration at 2% of diet caused decrease in yield grade from about 3.1 to about 2.9.

The seaweed extract administration also was shown to cause increase in actual preliminary yield grade from about 3.03 to about 3.19 (1% extract) and to about 3.14 (2% extract).

The seaweed extract administration also was shown to cause decrease in lean maturity from 67.5 to about 66.3 (1% extract) and to about 65.35 (2% extract).

The seaweed extract administration also was shown to cause increase in skeletal maturity from about 62.1 to about 73.8 (1% extract) and to about 69.7 (2% extract).

The seaweed extract administration was also shown to cause an increase in hot carcass weight in amount of about 50 pounds (1% extract) and about 15 pounds (2% extract).

The seaweed extract administration also was shown to improve weight gain over a 5-month period an amount of about 25 pounds per steer (1% extract) and about 55 pounds per steer (2% extract).

The seaweed extract administration did not appear to affect kidney, pelvic and heart fat amount (kPH).

EXAMPLE II

Two thousand five hundred and fifty cattle were fed in a feedlot, half in a control group and half in a treatment group. The treatment was 2% seaweed meal (Tasco™-14). The finishing period was about six months. The cattle weighed 450 to 480 pounds at the start of feedlot finishing and half were started on treatment at about 30 days into the finishing period when the cattle weighed almost 600 pounds. Feeding of seaweed meal to the treatment group was carried out for 14 days starting 30 days into the finishing period and for another 14 days at the end of the finishing period.

Figure 5:
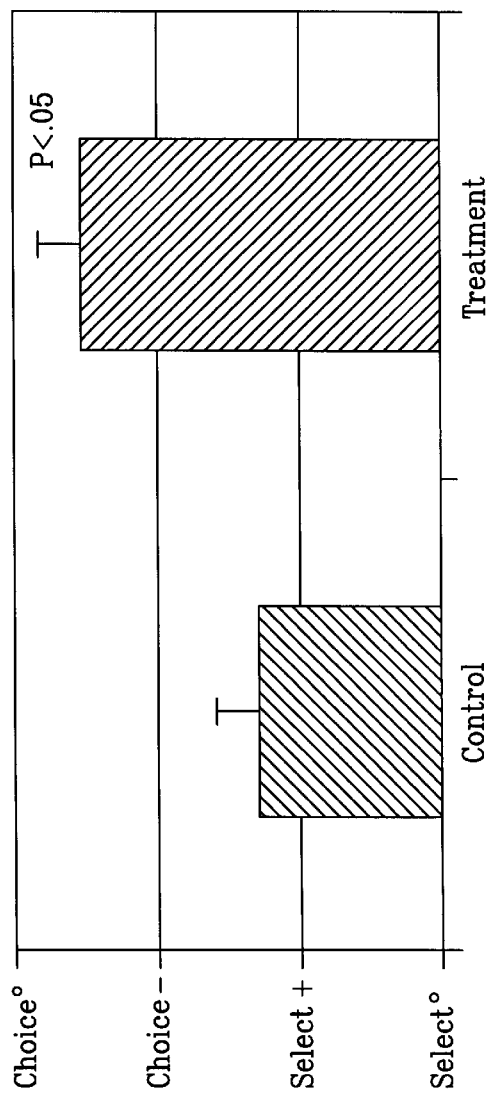
FIG. 5 depicts graphs showing quality grades obtained on direct feeding of seaweed meal at 2% of diet to cattle versus control and shows results of Example II.

Quality grade results were determined and are shown in FIG. 5. In FIG. 5, treatment is shown to cause increase in quality grade from select plus to choice minus.

Figure 6:
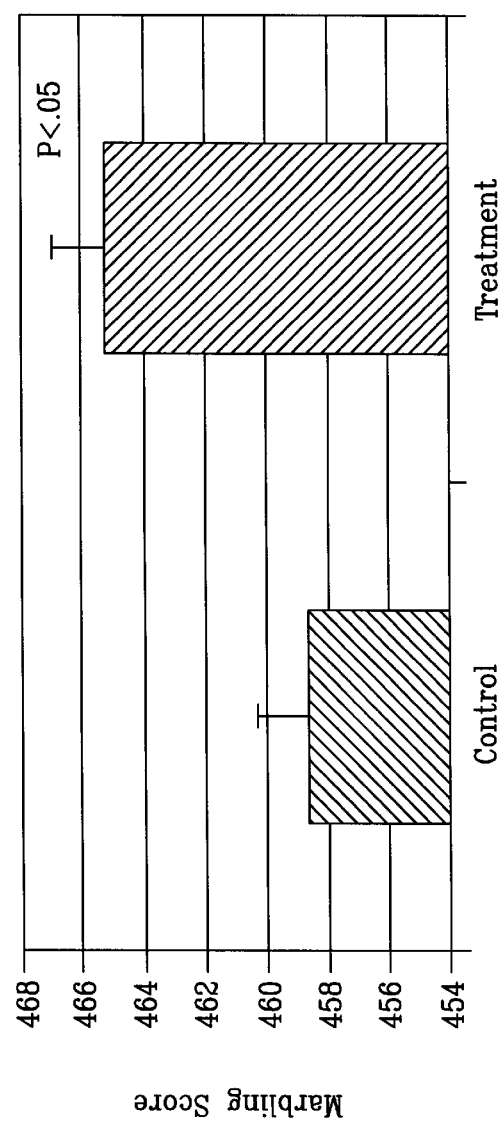
FIG. 6 depicts graphs showing marbling scores obtained on direct feeding of seaweed meal at 2% of diet to cattle versus control shows results of Example II.

Marbling score results were determined and are shown in FIG. 6. As shown in FIG. 6, treatment caused increase in marbling score from about 458 to about 465.

Figure 7:
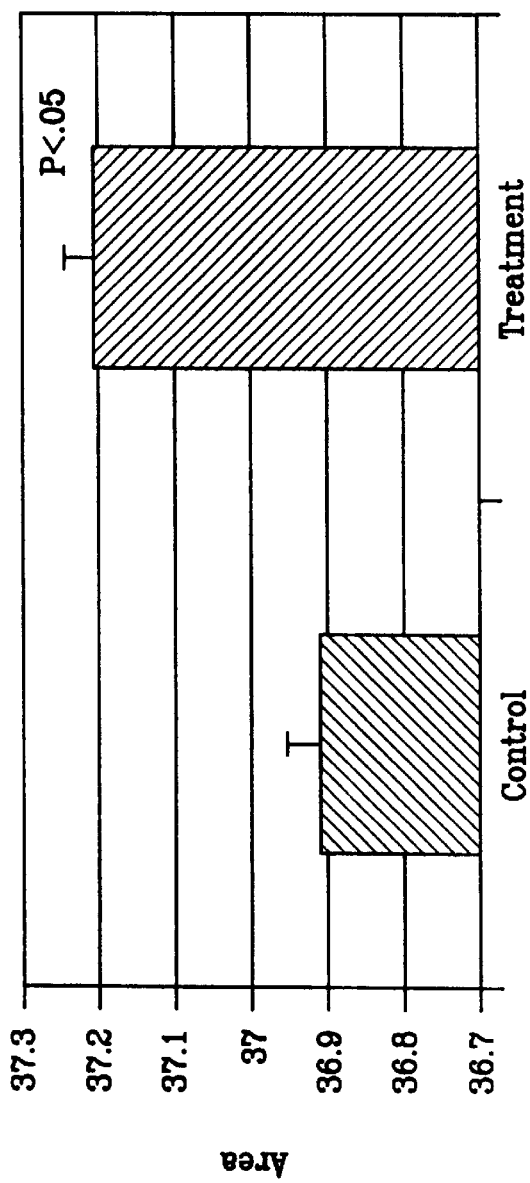
FIG. 7 depicts graphs showing ribeye area in square centimeters obtained on direct feeding of seaweed meal at 2% of diet to cattle versus control and shows results of Example II.
Figure 8:
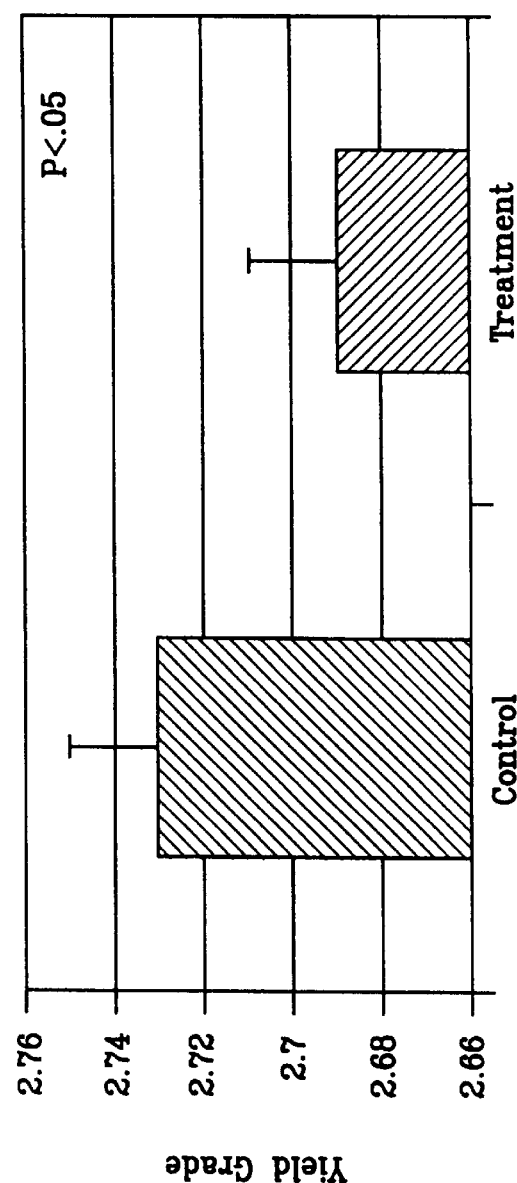
FIG. 8 depicts graphs showing yield grades obtained on direct feeding of seaweed meal at 2% of diet to cattle versus control and shows results of Example II.

Ribeye area results were determined and are shown in FIG. 7 in square centimeter. As shown in FIG. 7, treatment caused increase in ribeye area from about 36.9 square cm to about 37.2 square cm Yield grade results were determined and are shown in FIG. 8. As shown in FIG. 8, treatment caused reduction in yield grade.

Determinations also showed treatment caused reduction in average backfat from 0.50 inches to 0.47 inches.

Determinations showed treatment caused reduction in hot carcass weight.

The data showed Tasco™-14 significantly improved carcass merit.

There was a 0.4% increase in prime, a 5% increase in choice, a 3% decrease in standards, and a cost benefit of $325/pen (100 cattle).

EXAMPLE III

Sixty-four pigs were in the nursery phase of the life cycle for production (starting 28 days old and lasting three to five weeks).

The 64 pigs were divided into groups of four, and four groups each were fed either seaweed meal (Acadian Kelp Meal) in amount of 1% by weight of diet for the first 10 days of the nursery phase, seaweed extract (Acadian Soluble Seaweed Extract Powder) in amount of 1% by weight of diet for the first 10 days of the nursery phase, seaweed meal (Acadian Kelp Meal) in amount of 1% by weight of diet for five weeks, or a control diet. The diet referred to consisted by weight of 64.275% ground milo (sorghum), 32.5% soybean meal, 0.3% salt, 1.4% dicalcium phosphate, 1.1% calcium and 0.425% vitamins, and this was supplemented by 1% by weight of the total of magnesium oxide and 0.85% by weight of the total of trace minerals.

Evaluations were carried out for marbling, firmness and cooler shrink. Marbling results are shown in FIG. 9 where Tasco-Ex short means Tasco™s-Ex (powder form) for 10 days at 1% by weight of diet, Tasco-14 short mean Tasco™-14 for 10 days at 1% by weight of diet and Tasco-14 long means Tasco™ 14 for five weeks at 1% by weight of diet.

The results show seaweed supplement administration caused increase in marbling in two cases.

Figure 9:
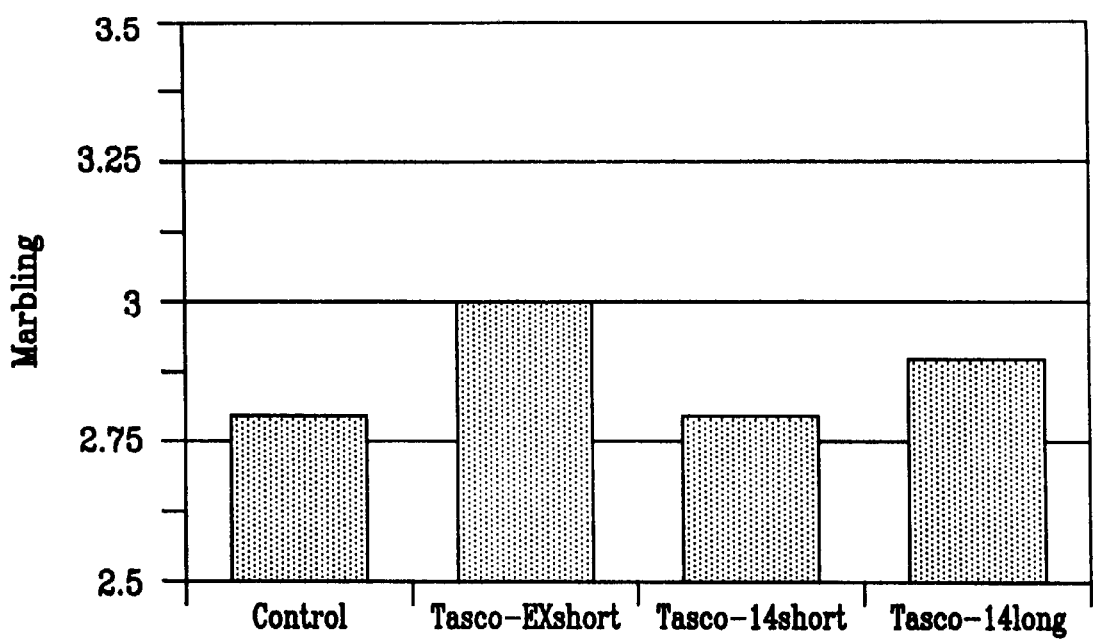
FIG. 9 depicts graphs showing marbling scores obtained on direct feeding of seaweed extract and seaweed meal to swine versus control for experiments described in Example III.
Figure 10:
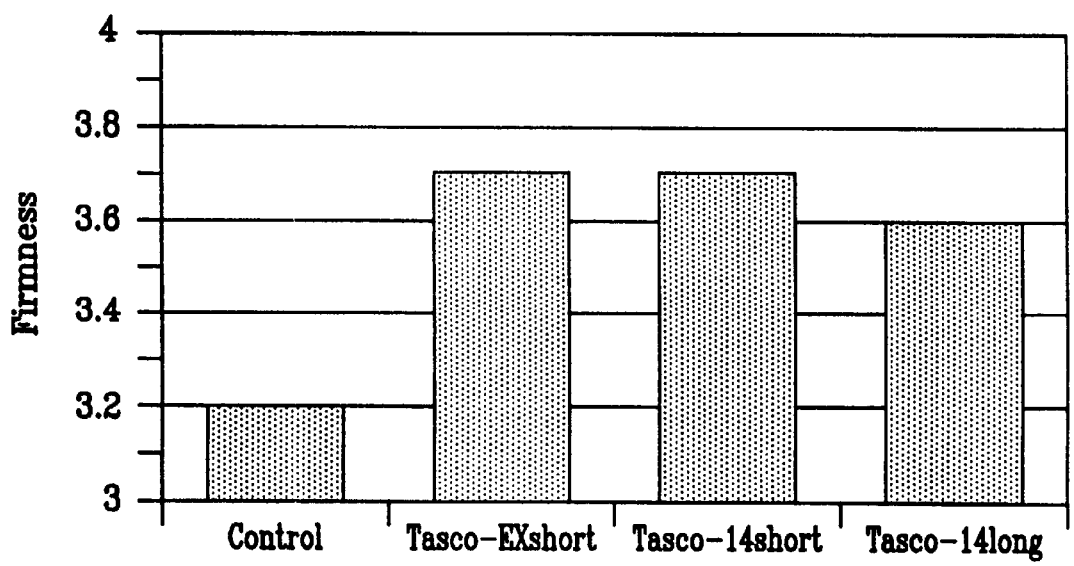
FIG. 10 depicts graphs showing firmness values obtained on direct feeding of seaweed extract and seaweed meal to swine versus control for experiments described in Example III.

Firmness results are shown in FIG. 10 where the same shorthand is used as for FIG. 9. The results show seaweed supplement caused increase in firmness in the three cases.

Figure 11:
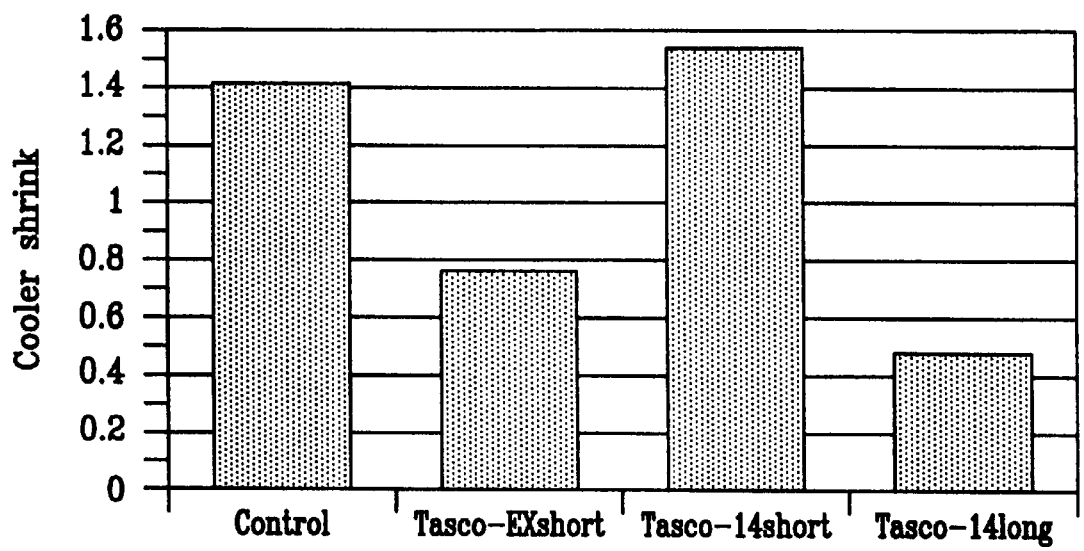
FIG. 11 depicts graphs showing cooler shrink values obtained on direct feeding of seaweed extract and seaweed meal to swine versus control for experiments described in Example III.

Cooler shrink results are shown in FIG. 11 where the same shorthand is used as for FIG. 9. The results show in two cases a reduction in cooler shrink.

Variations

Variation of the above will be obvious to those skilled in the art. Thus, the scope of the invention is defined by the claims.

What is claimed is:

1. A method of enhancing carcass quality in swine, comprising directly feeding seaweed supplement to swine in a carcass quality improving amount thereby to cause carcass quality improvement as manifested by increased marbling, increased firmness and decreased cooler shrink in meat obtained on slaughter compared to where seaweed supplement is not fed, and (b) determining at least one of marbling, firmness and cooler shrink wherein marbling score is increased at least 0.05, firmness is increased at least 0.2 and cooler shrinkage is decreased at least 0.2 compared to where seaweed supplement is not fed.

2. The method of claim 1 wherein the seaweed supplement is fed in an amount ranging from about 0.01 to 5% by weight of diet for 5 to 28 days.

3. The method of claim 2 wherein the seaweed supplement is seaweed meal.

4. The method of claim 2 wherein the seaweed supplement is seaweed extract.

5. The method of claim 1 where firmness is increased 0.5.

6. The method of claim 1 where firmness is increased 0.5 and cooler shrink is decreased 0.7.

7. The method of claim 1 where cooler shrink is decreased 1.0.

8. The method of claim 2 where the seaweed supplement is fed in an amount ranging from 0.5 to 1.5% by weight of diet.

9. The method of claim 2 where the seaweed supplement is from *A. nodosum*.

\* \* \* \* \*